(12) United States Patent
Carpenter et al.

(10) Patent No.: US 7,185,601 B2
(45) Date of Patent: Mar. 6, 2007

(54) CHEMICALLY SENSITIVE WARNING APPARATUS AND METHOD

(75) Inventors: Craig M. Carpenter, Boise, ID (US); Allen P. Mardian, Boise, ID (US); Philip H. Campbell, Meridian, ID (US); Ross S. Dando, Nampa, ID (US)

(73) Assignee: Micron Technology, Inc., Boise, ID (US)

(*) Notice: Subject to any disclaimer, the term of this patent is extended or adjusted under 35 U.S.C. 154(b) by 1034 days.

(21) Appl. No.: 09/798,672

(22) Filed: Mar. 1, 2001

(65) Prior Publication Data
US 2002/0121235 A1    Sep. 5, 2002

(51) Int. Cl.
*G01N 31/22* (2006.01)

(52) U.S. Cl. .............. 116/206; 116/DIG. 14; 422/87

(58) Field of Classification Search ........... 422/56, 422/57, 86, 87; 116/206, 207, DIG. 14, 209, 116/DIG. 1
See application file for complete search history.

(56) References Cited

U.S. PATENT DOCUMENTS

| | | | | |
|---|---|---|---|---|
| 3,047,405 A * | 7/1962 | Lanier | .............. | 374/106 |
| 3,386,807 A * | 6/1968 | Edenbaum | .............. | 422/56 |
| 3,523,011 A * | 8/1970 | Wacks et al. | .............. | 422/57 |
| 3,681,027 A * | 8/1972 | Smith | .............. | 436/117 |
| 4,205,043 A | 5/1980 | Esch et al. | .............. | 422/56 |
| 4,271,121 A * | 6/1981 | Diller et al. | .............. | 422/56 |
| 4,328,181 A * | 5/1982 | Anders et al. | .............. | 422/56 |
| 4,437,583 A * | 3/1984 | O'Connor | .............. | 222/108 |
| 4,597,942 A * | 7/1986 | Meathrel | .............. | 422/57 |
| 4,623,282 A * | 11/1986 | Allen | .............. | 405/157 |
| 4,643,588 A * | 2/1987 | Postle et al. | .............. | 374/160 |
| 4,699,838 A * | 10/1987 | Gilbert | .............. | 428/201 |
| 4,772,560 A * | 9/1988 | Attar | .............. | 436/165 |
| 5,019,453 A * | 5/1991 | Guerra | .............. | 428/518 |
| 5,158,363 A * | 10/1992 | Speelman et al. | .............. | 374/102 |
| 5,192,500 A * | 3/1993 | Treddenick | .............. | 422/56 |
| 5,217,444 A * | 6/1993 | Schoenfeld | .............. | 604/361 |
| 5,315,956 A * | 5/1994 | Reno | .............. | 116/216 |
| 5,538,170 A * | 7/1996 | Van Luit | .............. | 225/47 |
| 5,630,372 A * | 5/1997 | Ramsey et al. | .............. | 116/206 |
| 5,824,554 A * | 10/1998 | McKay | .............. | 436/20 |
| 6,175,310 B1 * | 1/2001 | Gott | .............. | 340/605 |
| 6,270,724 B1 * | 8/2001 | Woodaman | .............. | 422/58 |
| 6,284,198 B1 * | 9/2001 | Kirollos et al. | .............. | 422/87 |
| 2003/0033740 A1 * | 2/2003 | Perelli | .............. | 40/584 |

OTHER PUBLICATIONS

Scott Instruments, Dosimeter Badges [GMD Systems] Data Sheet in PDF format titled "GMD Ordering Guide 2000.p65", dated Feb. 27, 2001,as printed from their website on Aug. 29, 2006, p. 28 in particular—a color indicator, filter barrier, warning indicia, and color comparison.*

AFC International, Inc. website for K& M Environmental Passive Dosimetry Badges titled "SafeAir Direct Read Passive Monitoring Badges", dated Jan. 20, 2000, p. 1 showing a dose indicator badge with integral color comparison wheel.*

* cited by examiner

*Primary Examiner*—R. Alexander Smith
(74) *Attorney, Agent, or Firm*—Williams, Morgan & Amerson, P.C.

(57) ABSTRACT

A chemically sensitive warning apparatus capable of changing colors upon contact with a chemical is disclosed. The apparatus preferably comprises an elongated tape having opposed, first and second major surfaces and warning indicia visible to an individual viewing the first surface to provide visual indication of possible danger or hazardous condition. Mounted to the tape is at least one chemical indicator that is responsive to the presence of at least one chemical by changing colors so as to provide a visual indication of the exposure of the indicator to the chemical. The tape may also include at least one color reference indicia to facilitate interpretation of the color of the chemical indicator when the chemical indicator changes color upon exposure to the chemical.

32 Claims, 3 Drawing Sheets

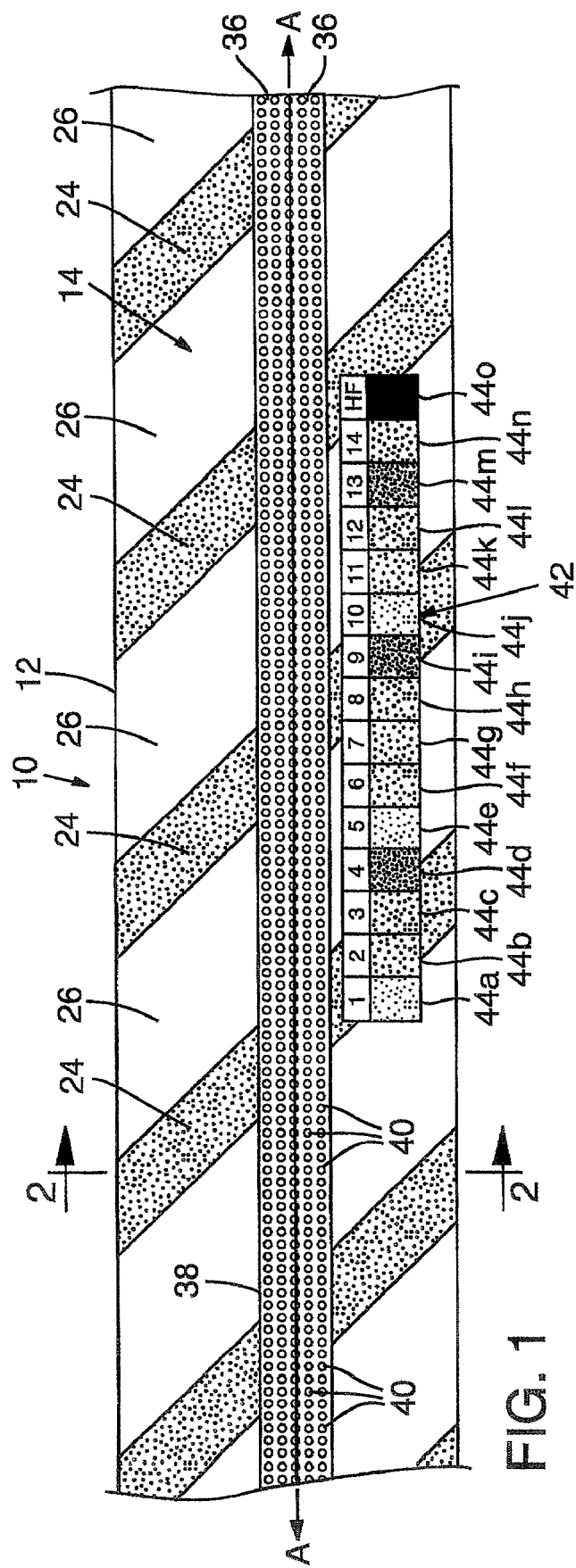
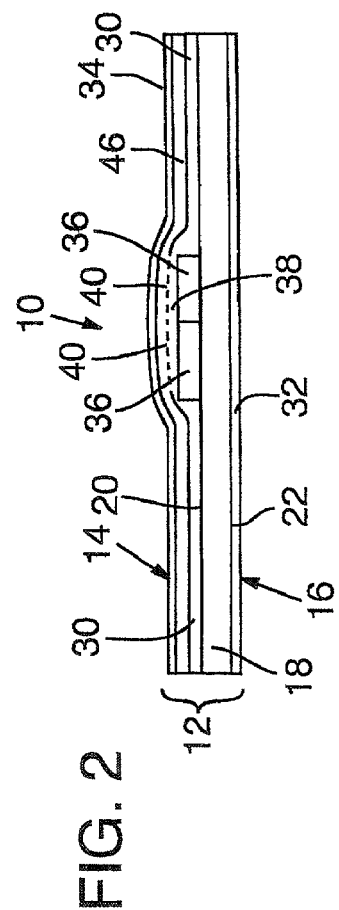
FIG. 1
FIG. 2

CHEMICALLY SENSITIVE WARNING APPARATUS AND METHOD

FIELD OF THE INVENTION

The present invention relates to a chemically sensitive warning apparatus for detecting and indicating the presence of hazardous chemicals.

BACKGROUND OF THE INVENTION

Warning devices, such as safety marking tape, are widely used in facilities to alert workers to the proximity of an area wherein potentially hazardous chemicals are used or stored. Traditional safety marking tape has on one side diagonal stripes of yellow and black bars for visual indication of a possible hazard and on the other side an adhesive coating to facilitate attachment of the tape to a surface. However, an actual chemical leak or spill may go undetected, as traditional safety tape is not capable of sensing the presence of hazardous chemicals. Thus, it is desirable to have a warning apparatus that is operable to provide visual indication of a hazard area and visual indication that the area has been contaminated by a chemical leak or spill.

SUMMARY OF THE INVENTION

According to one embodiment of the present invention, a chemically sensitive warning apparatus comprises a body having first and second major surfaces and warning indicia that are visible to an individual viewing the first surface to provide visual indication of a possible danger or hazard area. Mounted to the body in this embodiment is at least one chemical indicator that is operable to change colors upon exposure to a hazardous condition. The body desirably includes an adhesive carrying mounting surface to facilitate attachment of the body to a floor or other surface for use.

According to another embodiment of the invention, a chemically sensitive warning apparatus comprises a body carrying at least one chemical indicator that is operable to change colors upon exposure to a hazardous condition. The body also carries a color indicia to facilitate interpretation of the color of the chemical indicator when the chemical indicator is exposed to a hazardous condition.

In a desirable use of the invention, an elongated marker is positioned, such as on the floor of a building, to visually identify an area as a hazard area. If desired, the marker may be secured to the floor, such as with an adhesive. In the event that there is a hazardous condition in the area, such as a chemical spill, at least a portion of the marker changes colors to visually indicate spilling of the chemical. In another use of the invention, at least a major portion of a hazard area is surrounded with a marking tape and plural portions of the marking tape change colors to visually indicate spilling of a hazardous chemical in the hazard area. In yet another use of the invention, the hazard area is completely surrounded with the marking tape and at least a portion of the marking tape changes colors to visually indicate spilling of a hazardous chemical in the hazard area.

The present invention is directed toward new and nonobvious aspects of a chemically sensitive warning apparatus both alone and in combination with one another, as well as to nonobvious and unique methods relating thereto, as set forth in the claims below.

BRIEF DESCRIPTION OF DRAWING

FIG. 1 is a top plan view of a working embodiment of a chemically sensitive warning apparatus according to the present invention.

FIG. 2 is cross sectional view taken along line 2—2 of FIG. 1.

DETAILED DESCRIPTION OF THE INVENTION

Figure 3:
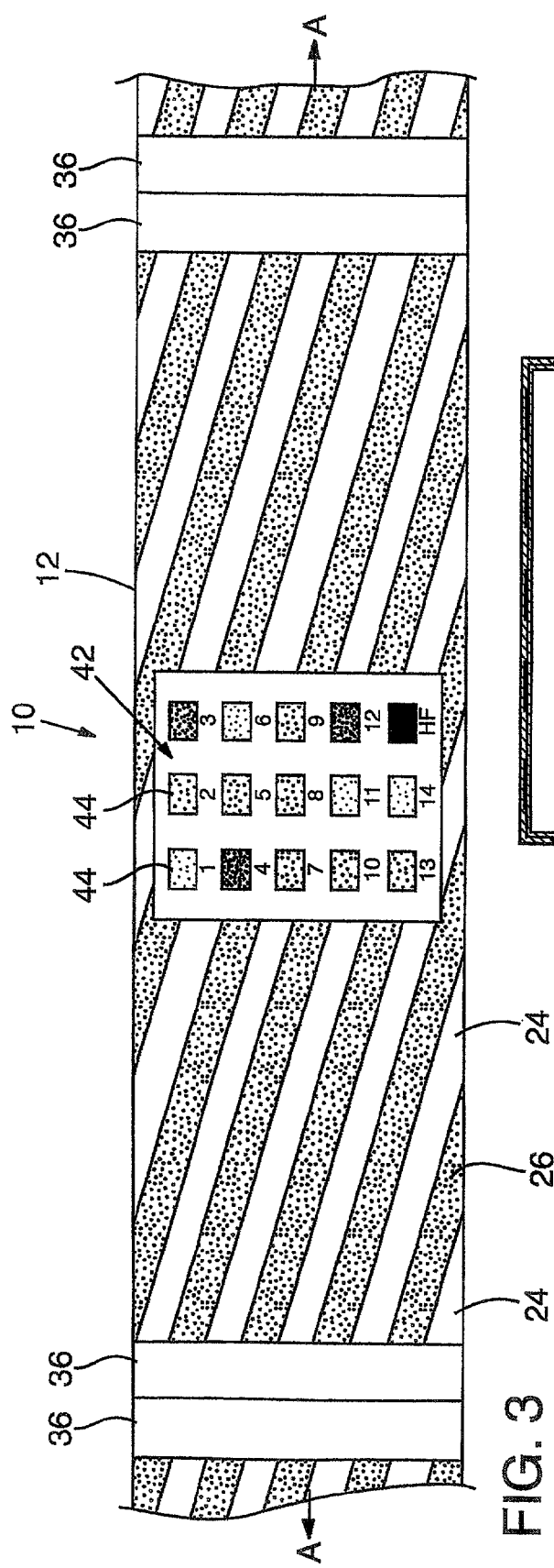
FIG. 3 is a top plan view of another embodiment of a chemically sensitive warning apparatus according to the present invention.

Referring to FIGS. 1 and 2, there is shown a chemically sensitive warning apparatus, color changing indicating assembly, or marker 10 for warning individuals of the presence of at least one chemical according to one embodiment of the present invention.

The illustrated form of warning apparatus 10 desirably comprises an elongated body 12 having a longitudinal axis A (as shown in FIG. 1) and first and second major surfaces 14 and 16 (as shown in FIG. 2). The particular shape of the body 12, however, is not limited to that of the illustrated embodiment. Accordingly, the body 12 may comprise any other geometric shape, such as a square or circle or any combination or variation thereof.

As shown in FIG. 2, the body 12 in the form shown comprises a plurality of layers, at least one of which is a base layer 18 having top and bottom surfaces 20 and 22. The body 12 may also include an overlay comprising a selectively permeable, transparent layer 30 at least partially overlaying the top surface 20 of the base layer 18. The layer 30 may be secured to the base layer 18, such as by the use of an adhesive. The body 12 carries in the embodiment shown at least one chemically sensitive indicator responsive to the presence of at least one chemical and may comprise plural side by side, elongated chemical indicators or chemical sensing strips 36 mounted to the body and operable to change colors when exposed to or upon contact with a hazardous chemical.

The chemical indicators 36 may be selected to change colors upon contact with the vapors given off by a chemical spill. Alternatively, the chemical indicators 36 may be operable to change colors only upon liquid contact with the spilled chemical (e.g., immersion or saturation of the chemical indicators by the liquid) or upon exposure to either liquid or vapor.

The chemical indicators 36 are desirably positioned on the top surface 20 of the base layer 18 and held in place by the selectively permeable layer 30 that is permeable to liquid and/or gas. The selectively permeable layer 30 may have a permeable portion 38 adjacent to and overlaying the chemicals indicators 36 to permit chemical contact with the chemical indicators 36 when there is a chemical spill. In the illustrated embodiment, the selectively permeable layer 30 comprises a plastic film having a permeable portion 38 provided with a plurality of perforations 40 to allow for such chemical contact. Other gas and/or liquid permeable materials may be used instead of an apertured film. In an alternative embodiment, the chemical indicators 36 may be secured to the top surface 20 of the base layer 18, such as with an adhesive applied to the bottom surface of the chemical indictors 36, in which case the warning apparatus 10 would be constructed without a permeable layer 30.

As shown in FIG. 1, the chemical indicators in this example, desirably extend continuously along at least a majority of the length of the body 12 in a direction parallel to the longitudinal axis A. In the context of this description, it is to be understood that "majority of the length" is defined as at least half of the length of the body. In other words, chemical indicators that extend continuously along at least a majority of the length of the body would extend continuously along for at least half of the length of the body. It is even more desirable to construct the warning apparatus 10 so that the chemical indicators 36 extend substantially continuously along or entirely along the entire length of the body 12. However, there is no requirement as to the exact length or even the number of chemical indicators used in the construction. Thus, the chemical indicators may extend continuously or non-continuously along a majority or less than a majority of the length of the body. Further, although the illustrated embodiment has been described as having plural, such as a pair of chemical indicators, the warning apparatus 10 may have any number of chemical indicators or even multiple pairs of chemical indicators. The chemical indicators do not have to extend in a direction parallel to the longitudinal axis A. Referring to FIG. 3, for example, there is shown another embodiment wherein pairs of chemical indicators 36 extend in a direction perpendicular to the longitudinal axis A of an elongated body 12 and each pair of chemical indicators is longitudinally spaced from an adjacent pair along the length of the body 12.

In the illustrated embodiment, one of the chemical indicators 36 comprises a pH sensitive material, such as a strip of pH paper, and the other chemical indicator comprises a strip of paper treated to indicate the presence of hydrofluoric acid. This arrangement is particularly useful for detecting the presence of commonly used acids and bases. It should be appreciated, however, that chemical indicators 36 may comprise any type of chemically sensitive material suitable for detecting the presence of hazardous chemicals. Without limitation, these may include materials such as litmus paper, lead acetate paper, potassium iodide/starch paper, or paper that is responsive to the presence of certain ions or gases. Further, it is to be understood that the apparatus 10 may include indicators that are responsive to other hazardous environmental conditions besides the presence of chemicals, such as the presence of particulate contaminants or the presence of radiation. In the latter case, a permeable cover may be omitted or an impermeable cover may be used.

The body 12 in this example also has safety markings or visual warning indicia, such as diagonal stripes of alternating colors 24 and 26 disposed on the top surface 20 of the base layer 18, that are visible to an individual viewing the first surface 14 of the body (as shown in FIG. 1). Alternatively, the safety markings may be provided on the selectively permeable layer 30 rather than on the base layer 18, in which case the selectively permeable layer need not be transparent to permit an individual to see the safety markings. In either case, the safety markings function to provide a visual indication of a possible danger or hazard area. Instead of the diagonal stripes shown in the illustrated embodiment, the safety markings may comprise any other shapes and/or symbols to provide visual indication of a possible danger. Still alternatively, the safety markings may comprise words or text for warning individuals of the existence of a possible danger. Possible examples include "Warning" or "Hazard Area". Such words or text may also describe the particular hazard or chemical that is being used in the area. Combinations of text and other visual indicia may also be used.

Also mounted to or carried by the body 12 in any suitable fashion, such as by an adhesive, in the illustrated embodiment, is at least one color reference indicia 42, in this case comprising a plurality of color samples 44a–o, to facilitate interpretation of the color of a chemical indicator 36 when the chemical indicator is exposed to a chemical. As are the chemical indicators 36, the color indicia 42 is desirably positioned on the top surface 20 of the base layer 18 and secured or otherwise held in place by the selectively permeable layer 30. If the body 12 is relatively long, it may be desirable to position a plurality of color indicia 42 along the length of the body 12 (see, e.g., FIG. 6).

As mentioned above, in the illustrated embodiment, one of the chemical indicators 36 may comprise a strip of pH paper and the other chemical indicator 36 may comprise a strip of paper treated to indicate the presence of hydrofluoric acid. Accordingly, each of color samples 44a–n may include a numerical indicia which corresponds to a numerical value on the pH scale to enable an individual to determine whether the pH paper has been exposed to an acid or a base and the strength of that acid or base (as shown in FIG. 1). In addition, color sample 44o, in this example, may have a color which matches the color that the chemical indicator for detecting hydrofluoric acid would become if exposed to hydrofluoric acid. Color sample or indicia 44o, as illustrated, may also be visually identified by the chemical symbol for hydrofluoric acid (HF, as shown in FIG. 1). Of course, the actual contents of a color indicia 42 for a particular embodiment will depend upon the type of chemical indicators used in that embodiment.

Referring again to FIG. 2, a removable, non-permeable, protective cover layer 46, desirably an adhesive tape, may overlay the top surface of the selectively permeable layer 30 to initially cover the permeable portion 38 of the selectively permeable layer 30 to prevent premature exposure or degradation of the chemical indicators 36 prior to installation. The top surface of the selectively permeable layer 30 may include a coating of a suitable release agent (not shown) to facilitate removal of the cover layer 46. The body 12 may also be provided with an adhesive carrying mounting surface, such as adhesive coating or layer 32 on the bottom surface 22 of the base layer 18, to facilitate attachment of the body to a surface. In this sense, the body 12 in one form is an elongated tape or marking tape, which may be wound around a core so as to form a roll of tape. In such a case, a release coating 34 may provided on the top surface of the cover layer 46 to facilitate detachment of the leading edge of the tape from the roll.

Figure 5:
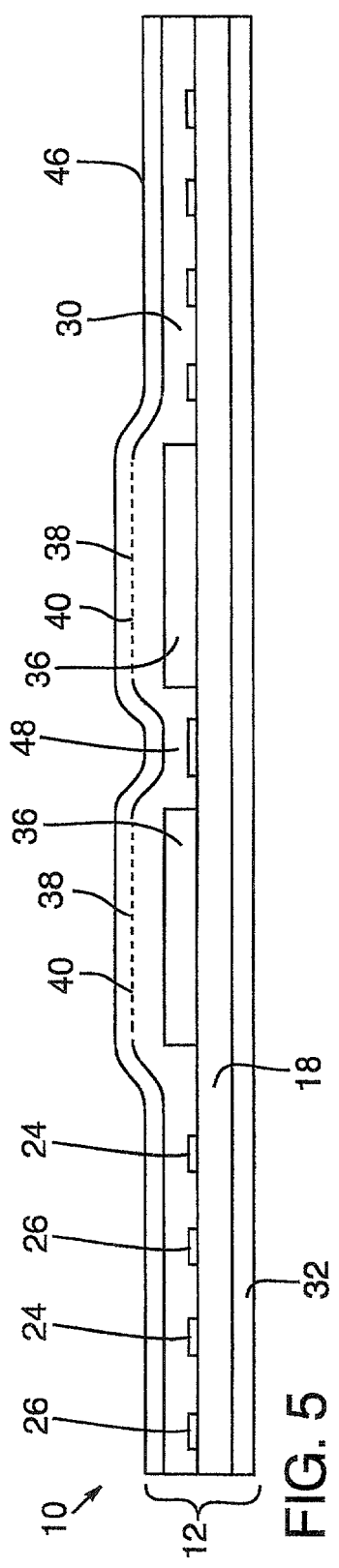
FIG. 5 is a cross sectional view taken along line 5—5 of FIG. 4.
Figure 4:
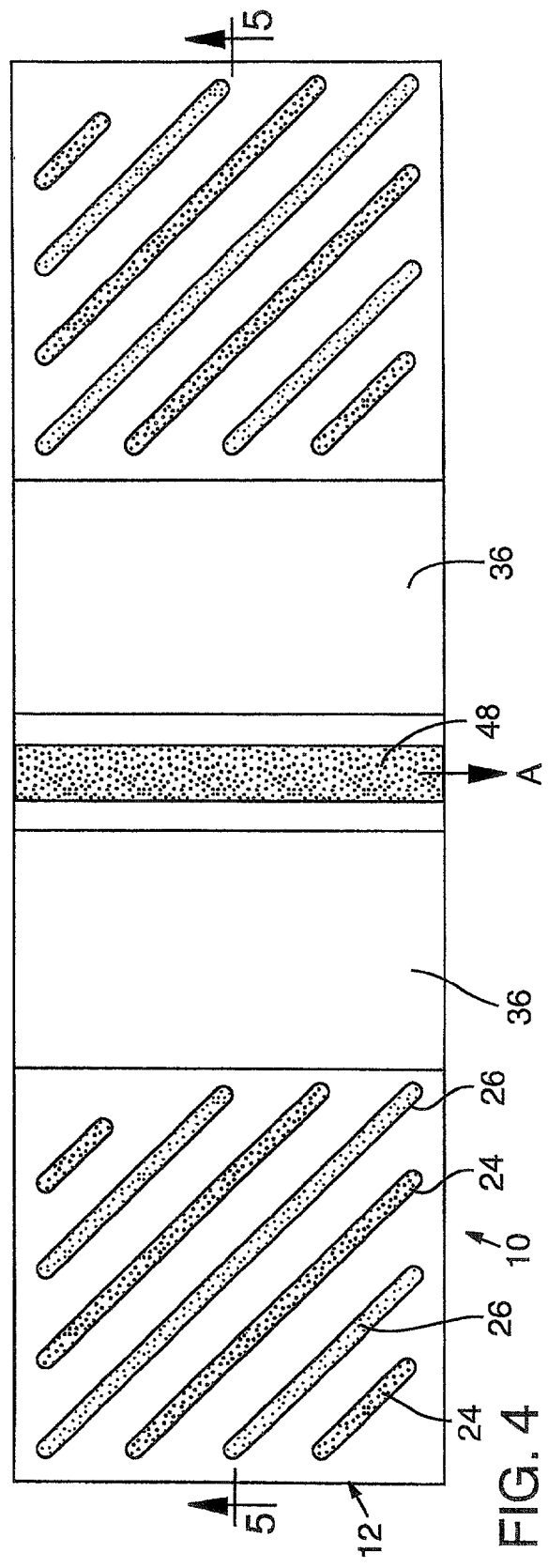
FIG. 4 is a top plan view of yet another embodiment of a chemically sensitive warning apparatus according to the present invention.

Referring to FIGS. 4 and 5, there is shown a warning apparatus 10 according to another embodiment of the invention. In this embodiment, two chemical indicators 36 extend in a direction parallel to the longitudinal axis A but are laterally spaced from each other and effectively separated by a portion 48 of the selectively permeable layer 30.

Figure 6:
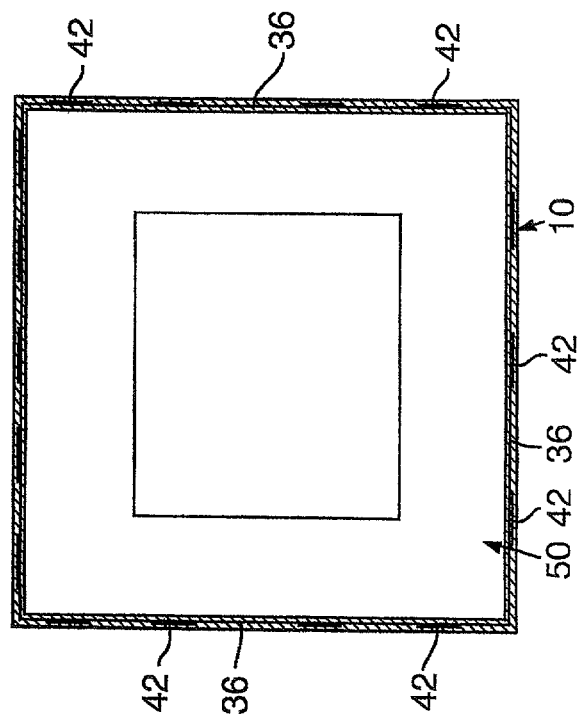
FIG. 6 is a top plan view showing a chemically sensitive warning apparatus of the present invention being used to mark off the boundary of a hazard area.

An exemplary method of use of the warning apparatus 10 is shown in FIG. 6. The warning apparatus 10 is positioned, such as on the floor of a building or other surface, to visually identify a hazard area 50 where hazardous chemicals are being used or stored. As shown in FIG. 6, the warning apparatus 10 is desirably positioned so as to completely surround the hazard area 50 to provide visually indication of the boundary of the hazard area. However, it is not required that the warning apparatus 10 entirely surround the hazard area 50. Thus, the warning apparatus 10 may surround at least a major portion of the hazard area 50 or less than a major portion of the hazard area 50.

If, as described above, the warning apparatus 10 comprises an elongated marking tape, it may be adhesively secured to the floor of the hazard area 50. The warning apparatus may also be secured or otherwise held to the floor by means other than an adhesive, such as with mechanical fasteners, however it is not a required that the warning apparatus be held down or secured to the floor. In the event that there is a hazardous condition in the area, such as a chemical spill, at least a portion or plural portions of the warning apparatus 10, such as a portion or portions of chemical indicator 36 in the illustrated embodiment, changes colors upon exposure to the chemical to visually indicate spilling of the chemical. Consequently, an individual will be able to quickly identify the spilled chemical by comparing the color change to the color samples provided on one of the color indicia 42 and then commence an appropriate decontamination process.

The present invention has been shown in the described embodiments for illustrative purposes only. The present invention may be subject to many modifications and changes without departing from the spirit or essential characteristics thereof. We therefore claim as our invention all such modifications as come within the spirit and scope of the following claims.

We claim:

1. A chemically sensitive warning apparatus comprising:
   a body having opposed, first and second major surfaces, the body having at least one first indicator comprising first warning indicia visible to an individual viewing the first surface to provide a visual indication of a possible danger, said first warning indicia comprising a repeating pattern of markings along the majority of the length of the body;
   at least one second indicator, different from the first indicator, the at least one second indicator comprising at least one chemical indicator mounted to the body and responsive to the presence of at least one chemical to provide a visual indication of the exposure of the chemical indicator to the at least one chemical, the visual indication being visible to an individual viewing the first surface; and
   a transparent layer overlaying the at least one second indicator and adhering directly to the first surface, the transparent layer being made of a fluid-impermeable material having perforations adjacent the at least one second indicator to allow a chemical to contact the at least one chemical indicator through the transparent layer.

2. A chemically sensitive warning apparatus comprising:
   a body having opposed, first and second major surfaces, the body having warning indicia visible to an individual viewing the first surface to provide visual indication of a possible danger; and
   at least one chemical indicator mounted to the body and responsive to the presence of at least one chemical to provide a visual indication of the exposure of the chemical indicator to the at least one chemical;
   wherein the body comprises plural layers, at least one of which is a base layer and another of which is an overlay layer positioned to overlay the base layer, the overlay layer comprising a selectively permeable, transparent layer and having a permeable portion adjacent the chemical indicator, and wherein the warning indicia comprises colored stripes of alternating colors on the base layer.

3. The chemically sensitive warning apparatus according to claim 2 further comprising a removable protective layer overlaying the selectively permeable layer.

4. The chemically sensitive warning apparatus according to claim 1 wherein the at least one chemical indicator is a pH sensitive material.

5. A chemically sensitive warning apparatus comprising:
   a body having opposed, first and second major surfaces, the body having a first indicator comprising warning indicia visible to an individual viewing the first surface, the warning indicia comprising a repeating pattern of markings along the majority of the length of the body for warning individuals of the existence of a possible danger;
   a second indicator comprising at least one chemical indicator mounted to the body and operable to change colors upon exposure to at least one chemical; and
   at least one color indicia mounted to the body to facilitate identification of the at least one chemical when the at least one chemical contacts and causes the second indicator to change colors.

6. The chemically sensitive warning apparatus of claim 5 wherein the at least one color indicia comprises a plurality of color samples, each of which has a numerical indicia which corresponds to a numerical value on the pH scale.

7. A method for warning individuals of a chemical spill in a hazard area, the method comprising:
   adhesively securing an elongated marking tape to a floor so as to extend continuously along a major portion of the boundary of the hazard area, the marking tape having warning indicia to provide a visual indication of a possible hazard in the hazard area, the warning indicia comprising a repeating pattern of markings along the majority of the length of the tape; and
   changing the color of at least a portion of the marking tape to visually indicate spilling of a hazardous chemical in the hazard area.

8. The method of claim 7 wherein the act of securing the marking tape to the floor comprises surrounding at least a major portion of the hazard area with the marking tape and the act of changing color comprises the act of changing the color of plural portions of the marking tape.

9. The method of claim 8 wherein the marking tape has a strip of chemically sensitive material extending continuously along the length of the marking tape, the strip of chemically sensitive material being operable to change colors upon exposure to a spilled chemical in the hazard area.

10. The method of claim 7 wherein the marking tape has at least one strip of chemically sensitive material and a transparent layer positioned to overlay the strip of chemically sensitive material.

11. An apparatus for warning individuals of a chemical spill in a hazard area comprising:
   a body comprising at least one layer having first and second surfaces, the first surface having safety markings comprising a repeating pattern of markings along the majority of the length of the body, which provide visual indication of a possible danger in the absence of a chemical spill, and at least one chemical indicator carried by the body adjacent the safety markings, the chemical indicator being operable to change color upon contact with a spilled chemical;

wherein the body comprises a roll of elongated material, which can be unwound and positioned on a floor or structure when the apparatus is used.

12. An apparatus according to claim 11 wherein the roll of elongated material comprises a roll of elongated tape having an adhesive carrying mounting surface for mounting the apparatus to a floor or structure, the chemical indicator comprising at least one elongated chemical sensing strip.

13. An apparatus according to claim 12 wherein the at least one elongated chemical sensing strip extends continuously along at least a majority of the length of the tape, and the body further comprises a non-permeable transparent layer positioned to overlay the sensing strip, the transparent layer having a plurality of perforations extending substantially along the entire length of the tape adjacent the sensing strip to allow a spilled chemical to contact the sensing strip.

14. An apparatus according to claim 12 wherein the chemical indicator comprises at least two side by side elongated chemical sensing strips.

15. An apparatus according to claim 14 wherein the body has a longitudinal axis and the at least two side by side chemical sensing strips are elongated to extend in a direction parallel to the longitudinal axis.

16. An apparatus according to claim 14 wherein the body has a longitudinal axis and the at least two side by side chemical sensing strips are elongated to extend in a direction perpendicular to the longitudinal axis.

17. An apparatus for warning individuals of the presence of at least one chemical in a hazard area comprising:
a body comprising at least one layer having first and second surfaces, the first surface having safety markings, which provide visual indication that at least one chemical is stored or used in the hazard area, the safety markings comprising a repeating pattern of markings along the majority of the length of the body, the first surface also having at least one chemical indicator carried by the body adjacent the markings, the chemical indicator being operable to change color upon contact with a chemical; and
a transparent layer adhering to the first surface of the at least one layer and being permeable in a portion overlapping the at least one chemical indicator.

18. An apparatus for warning individuals of the presence of at least one chemical in a hazard area comprising:
a body comprising at least one layer having first and second surfaces, the first surface having markings, which provide visual indication that at least one chemical is stored or used in the hazard area, and at least one chemical indicator carried by the body, the chemical indicator being operable to change color upon contact with a chemical; and
a transparent layer adhering to the first surface of the at least one layer and being permeable in a portion overlapping the at least one chemical indicator;
wherein the markings comprise stripes of alternating colors, the at least one chemical indicator comprises at least two elongated chemical indicators spaced apart from each other so that a portion of the transparent layer is disposed between the two chemical indicators, and the apparatus further comprises a removable cover adhering to the transparent layer which may be removed after the apparatus is installed.

19. A color changing indicating assembly for indicating hazardous conditions comprising:
a base layer having opposed, first and second major surfaces;
at least one chemical indicator carried by the first major surface of the base layer and capable of changing colors when exposed to a hazardous condition, the change in color being visible to an individual viewing the first major surface;
at least one color indicia comprising a plurality of color samples carried by the first major surface of the base layer and visible to an individual viewing the first major surface to facilitate interpretation of the color of the chemical indicator when it becomes exposed to a hazardous condition; and
warning indicia comprising a repeating pattern of markings along the length of the assembly that warn individuals of the existence of a possible danger.

20. A color changing indicating assembly for indicating hazardous conditions comprising:
a base layer having opposed, first and second major surfaces;
at least one chemical indicator carried by the first major surface of the base layer and capable of changing colors when exposed to a hazardous condition, the change in color being visible to an individual viewing the first major surface; and
at least one color indicia carried by the first major surface of the base layer and visible to an individual viewing the first major surface to facilitate interpretation of the color of the chemical indicator when it becomes exposed to a hazardous condition, wherein the at least one chemical indicator is mounted directly to the first surface of the base layer and the base layer has safety stripes on the first major layer thereof providing a visual indication of a possible danger.

21. The assembly of claim 19 further comprising a transparent layer adhering directly to the first surface of the base layer and having a plurality of perforations adjacent the indicator.

22. The assembly of claim 19 further comprising a liquid permeable layer adhering to the first surface of the base layer and through which at least a portion of the chemical indicator is visible at least when the color change occurs upon exposure to a hazardous condition.

23. The assembly of claim 19 wherein the base layer is a roll of elongated tape having an adhesive coating on the second surface, wherein the tape can be unrolled and adhesively secured to a floor or other surface to mark off the boundary of a hazard area.

24. The assembly of claim 19 wherein the indicator is operable to detect the presence of hydrofluoric acid.

25. A chemically sensitive warning apparatus comprising:
a base layer having opposed, first and second major surfaces;
at least one strip of chemically sensitive material positioned on and extending along the length of the first surface of the base layer;
a selectively permeable, transparent layer adhering directly to the first surface of the base layer and having a plurality of perforations at least adjacent to a portion of the strip of chemically sensitive material;
wherein the selectively permeable layer is a film that is non-permeable to fluids and has perforations extending along the length of the base layer adjacent the strip of chemically sensitive material; and
warning indicia comprising a repeating pattern of markings along the majority of the length of the apparatus; that warn individuals of the existence of a possible danger without identifying any chemicals that may be detected by the chemically sensitive material.

26. An apparatus according to claim 25 wherein the at least one strip of chemically sensitive material comprises at least two strips of chemically sensitive material positioned on and being elongated to extend along the length of the first surface of the base layer, one of which is pH paper and the other of which is selected to detect the presence of hydrofluoric acid.

27. An apparatus according to claim 26 wherein the first surface of the base layer has warning markings, which provide a visual indication of the existence of a hazard area, and the two strips of chemically sensing material are spaced apart from each other in a direction perpendicular to the length of the base layer so that a portion of the transparent layer is disposed between and separates the two strips of chemically sensing material.

28. A color changing indicating assembly for indicating hazardous conditions comprising:
   first indicating marking means for providing a visual indication of a hazard area, said first indicating marking means comprising stripes of alternating colors;
   second indicating means, separate from the first indicating marking means, for changing colors when exposed to a hazardous condition; and
   means for supporting the first and second indicating means.

29. The assembly of claim 28 further comprising means for protecting the second indicating means from exposure to hazardous conditions prior to installation.

30. The assembly of claim 28 further comprising color interpreting means for use in interpreting the color of the second indicating means when exposed to a hazardous condition.

31. The assembly of claim 28 wherein the means for supporting the first and second indicating means comprises means for attaching the assembly to a surface.

32. Chemically sensitive safety tape comprising:
   a base layer having opposed, first and second major surfaces, the second surface having an adhesive coating to facilitate attachment of the tape to a surface, the first surface having a first indicator comprising a repeating pattern of safety markings along the length of the first surface to provide visual indication of the existence of a hazard area;
   a second indicator comprising at least one chemical indicator positioned on and extending along a length of the first surface of the base layer adjacent the first indicator;
   at least one color indicia disposed on the first surface of the base layer to facilitate interpretation of the color of the chemical indicator when a chemical comes into contact therewith;
   a transparent layer adhering to the first surface of the base layer to maintain the chemical indicator and color indicia on the first surface of the base layer, the transparent layer having perforations adjacent the chemical indicator; and
   a removable protective layer adhering to the transparent layer to cover the perforations and prevent premature exposure of the chemical indicator prior to installation.

* * * * *